United States Patent [19]

Gardano et al.

[11] Patent Number: 4,885,409

[45] Date of Patent: Dec. 5, 1989

[54] PROCESS FOR THE HYDROGENATION OF BIS-PHENOLS

[75] Inventors: Andrea Gardano, Trino Vercellese; Francesco Casagrande, Novara; Marco Foä, Novara; Guido Petrini, Novara Galliate; Riccardo Barisone, Novara; Lawrence Chapoy, Lesa, all of Italy

[73] Assignee: Montedison S.p.A., Milan, Italy

[21] Appl. No.: 190,049

[22] Filed: May 4, 1988

[30] Foreign Application Priority Data

May 5, 1987 [IT] Italy ................................ 20368 A/87

[51] Int. Cl.[4] .............................................. C07C 35/21
[52] U.S. Cl. .................... 568/834; 568/814; 568/819; 568/822; 568/832; 568/833; 568/835
[58] Field of Search ............... 568/814, 832, 833, 834, 568/835, 816, 819, 822, 817

[56] References Cited

U.S. PATENT DOCUMENTS

| | | | |
|---|---|---|---|
| 1,771,089 | 7/1930 | Jordon | 568/832 |
| 3,959,382 | 5/1976 | Yeh et al. | 568/835 |
| 4,212,990 | 7/1980 | Yasahara et al. | 568/832 |
| 4,508,918 | 4/1985 | Yasahara et al. | 568/832 |
| 4,551,564 | 11/1985 | Otte et al. | 568/832 |

FOREIGN PATENT DOCUMENTS

| | | | |
|---|---|---|---|
| 478018 | 10/1951 | Canada | 568/832 |
| 478463 | 11/1951 | Canada | 568/832 |
| 3401343 | 5/1985 | Fed. Rep. of Germany | 568/834 |

OTHER PUBLICATIONS

Ungnade et al., "Jour. Amer. Chem. Soc.", vol. 66, pp. 118–122 (1944).

*Primary Examiner*—Werren B. Lone
*Attorney, Agent, or Firm*—Stevens, Davis, Miller & Mosher

[57] ABSTRACT

Process for the hydrogenation of bis-phenols by reacting bis-phenols with hydrogen in the presence of a catalytic system consisting of palladium supported on activated carbon.

10 Claims, No Drawings

PROCESS FOR THE HYDROGENATION OF BIS-PHENOLS

DESCRIPTION OF THE INVENTION

The present invention relates to a process for the hydrogenation of bis-phenols.

More particularly, the present invention relates to a process for the preparation of products of the formula:

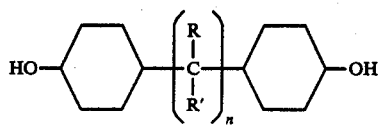

wherein R and R', equal to or different from each other, are hydrogen or $C_1$–$C_{10}$-alkyl radicals and n is 0 or 1, by catalytic hydrogenation of the corresponding aromatic derivatives of the formula:

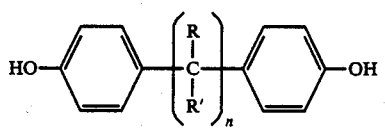

wherein R, R' and n have the above meanings.

Products of formula (I) wherein n=1 are known compounds, generally used as comonomers for the preparation of thermosetting polyester resins, and especially when both substituents R and R' are methyl groups.

It is also known that of these products at least three stereoisomeric forms are possible, which differ among themselves as to the reciprocal position of the alcoholic hydroxyl groups with reference to the radical —C(RR'—)—, generally in equatorial (para) position in respect of the two cyclohexane rings.

In particular, the trans-trans stereoisomer, which shows both the hydroxyl gruops in equatorial position, has been used to obtain high molecular weight polyesters showing good mechanical properties (Journal of Polymer Science, Vol. 24, pages 419–426 (1986)).

Compounds of formula (I) wherein n=0 showing trans-trans stereoisomery are used as intermediate compounds for the synthesis of liquid crystals.

Therefore it is interesting from an industrial point of view to have available a process for the preparation of compounds of the formula (I) which will allow one to obtain an isomeric mixture rich in the trans-trans isomer.

Furthermore, it is also interesting that this process allows one to obtain the above-mentioned products with a high degree of purity while reducing as much as possible the presence of monofunctional derivatives which stop the growth of polymer chains in condensation reactions and represent impurities which can be removed only with difficulty.

A process for the preparation of products having the formula (I) wherein n=1 is described in U.S. Pat. No. 4,503,273. According to that patent the above-mentioned products can be otained by hydrogenation of the corresponding aromatic derivatives in the presence of a catalytic system preferably consisting of nickel supported on a solid acidic diluent such as silica, alumina, silica-alumina, etc. Promoter of that catalytic system is a combination of a non-aqueous organic solvent with a base chosen from oxides, hydroxides, or carbonates of alkali or alkaline-earth metals.

The drawback of that process, and in particular of the corresponding catalytic system, is that the hydrogenation reaction has a selectivity as to a useful hydrogenated product lower than 95% by mols, with a maximum ratio among the trans-trans isomers and cis-cis and cis-trans isomers about equal to 1 or in some cases, lower than 1.

Futhermore, the highest yield as to the trans-trans isomer is obtained with prejudice to the selectivity of reaction.

The presence of impurities, in particular the presence of mono-hydroxylated derivatives, makes it necessary to purify the reaction mixture in order to use it in the synthesis of high molecular weight polyesters.

Analogous problems have been found with catalysts consisting of ruthenium supported on carbon, nickel on diatomite, or Raney nickel as described in Japanese Pat. Appln. No. 78/119855. As a matter of fact, by the use of the above-mentioned catalysts, there are obtained either low selectivity as to the trans-trans isomer when the ruthenium catalyst is used, or selectivity as to useful hydrogenated product lower than 90%, when the nickel catalysts are used.

Products of formula (I) wherein n=0 are described in the "Journal of the American Chemical Society", Vol. 76, page 1733 (1954), and are prepared by hydrogenation of the corresponding bis-phenol with Raney nickel catalysts, but unsatisfactory yields are obtained.

It has now been found, in accordance with the present invention, that products having the formula (I) with a high degree of purity and a trans-trans isomer content higher than 55% by weight may be obtained by a hydrogenation of the corresponding hydroxy-substituted aromatic derivatives, which process uses a hydrogenation catalyst supported on activated carbon.

Therefore, the object of the present invention is a process for the hydrogenation of bis-phenols, comprising reacting bis-phenols with hydrogen in the presence of a catalytic system consisting or consisting essentially of palladium on activated carbon.

Examples of suitable bis-phenols are: 4,4'-dihydroxydiphenyl, 1,1-bis(4-hydroxyphenyl)ethane, 2,2-bis(4-hydroxyphenyl)-propane, 2,2-bis(4-hydroxyphenyl)butane, 3,3-bis(4-hydroxyphenyl)hexane, etc. The preferred bis-phenols are: 2,2-bis(4-hydroxyphenyl)propane and 4,4'-dihydroxydiphenyl.

The activated carbon used as supporting material for the palladium is a per se known product and has a specific surface lower than 1000 $m^2/g$, in particular a surface between 400 and 900 $m^2/g$, and preferably a surface between 600 and 800 $m^2/g$.

The catalytic system may be prepared by any one of the general methods which can be found per se in the literature.

For instance, an acid solution of a palladium halide, e.g., the chloride, is added to an alkaline suspension of powdered activated carbon the size of the particles being, at least for 80% by weight, lower than 40 micrometers.

After having completed the addition, the hydrolysis compounds deposited on the carbon are transformed into metal derivatives by treatment with a reducing agent at a temperature between 20° and 90° C. Reducing agents particularly suitable for this purpose are sodium hypophosphite and sodium formate.

The solid product is then recovered by filtration and washed with water at temperature between 20° and 100° C. until the halide is removed.

The final catalyst, which contains about 50% b.w. of water, may be used as such or it may be previously dried.

According to a preferred embodiment of the present invention, the thus-obtained catalytic system preferably contains a small amount of alkali so as to provide a pH higher than 7 if dispersed in water. For this reason, it is preferable to treat the final catalyst with a solution of a salt of an alkali or alkaline-earth metal.

The content of palladium in the catalytic system is not critical and is preferably between 1 and 20% by weight, calculated on the dry catalyst. However, concentrations higher than 20% b.w. may be used.

The hydrogenation reaction may take place in bulk or in a solvent optionally additioned with water. As solvent an organic solvent is preferably used selected from esters, ethers, alcohols, saturated or cyclic having a boiling point higher than 50° C., saturated or cyclic hydrocarbons containing from 5 to 20 carbon atoms, etc.

Particularly suitable are ethyl acetate, methyl-t-butylether and ethanol, either alone or additioned with water up to 2% by volume, and cyclohexane.

Reaction temperature is between 80° and 160° C., and the hydrogen pressure is between 50 and 150 atm, preferably between 80 and 120 atm.

The process of the present invention allows one to obtain products having the formula (I) with a high degree of purity, in that reaction selectivity is higher than 99% b.w., and with a trans-trans isomer content higher than 55% b.w., and generally higher than 60%.

In order still better to understand the present invention and to practically perform the same, some illustrative but not limiting examples are now reported.

EXAMPLE 1

In a 1 liter stainless steel autoclave 40 g of 2,2-bis(4-hydroxyphenyl)propane (Bisphenol A), 500 ml of ethylacetate, and 44 g of catalyst consisting of activated carbon, having a specific surface of about 750 m$^2$/g, and containing 50% b.w. of water and supporting 5% b.w. of palladium calculated on the dry catalyst are introduced.

After having closed the autoclave and washing with nitrogen to expel the air, 80 atm of hydrogen are introduced. By keeping the autoclave under stirring, the temperature is raised to 140° C. and the pressure rises to 100 atm.

The whole is kept at 140° C. for 12 hours, by replacing the hydrogen absorbed with fresh hydrogen in order to maintain a pressure of 100 atm. After having cooled to room temperature, the remaining pressure is discharged and the contents of the autoclave are washed with nitrogen.

The suspension is discharged and the whole is completely dissolved by adding 500 ml of ethanol.

The whole is filtered on paper to recover the catalyst which is washed with ethanol. The clear solution is evaporated thus obtaining 43.2 g of hydrogenated bisphenol A with a 99.7% yield (conversion 100%, selectivity 99.7%).

By the gas chromatographic analysis of the crude reaction product (capillary column of molten silica bonded phase SPB1 30M 1.0 mm 0.32 mm ID SUPELCO INC.) the isomeric composition of the hydrogenated bisphenol A turns out to be 62.6% trans-trans; 32.5% cis-trans; 4.9% cis-cis.

EXAMPLE 2

This example is performed by operating as described in Example 1 using as substrate 4,4'-dihydroxydiphenyl and ethyl acetate containing 1% of water as solvent. 42.4 g of 4,4'-dihydroxydicyclohexyl are obtained with a 99.5% yield (conversion 100%, selectivity 99.5%).

By the gas chromatographic analysis of the crude reaction product the isomeric composition is found to be as follows: 60.2% trans-trans; 34.6% cis-trans; 5.2% cis-cis.

EXAMPLE 3

The catalyst used in Example 1 was dried at 110° C. to constant weight. 2 g of this catalyst was used by working under the same conditions as in Example 1.

Hydrogenated Bisphenol A is obtained with a practically quantitative yield (higher than 99.5%).

By the gas chromatographic analysis of the crude reaction product the isomeric composition was found to be as follows; 57.2% trans-trans; 36.3% cis-trans; 6.5% cis-cis.

EXAMPLE 4

By working as described in Example 1, using a catalyst (palladium on 5% activated carbon containing 50% of water) prepared by using carbon having a specific surface of about 600 m$^2$/g, hydrogenated Bisphenol A is obtained with practically quantitative yield (higher than 99.5%).

By gas chromatographic analysis of the crude reaction product the isomeric composition was found to be as follows: 56.0% trans-trans; 37.2% cis-trans; 6.8% cis-cis.

EXAMPLE 5

By working as described in Example 1, using a catalyst (palladium on 5% carbon containing 50% water) washed with acid to remove ashes and thereafter washed again with an aqueous solution containing 1.5% of sodium carbonate, hydrogenated Bisphenol A is obtained with practically quantitative yield (higher than 99.5%). By the gas chromatographic analysis of the crude reaction product, the isomeric composition was found to be as follows: 63.2% trans-trans; 31.7% cis-trans; 5.1% cis-cis.

EXAMPLE 6

This example is carried out by working as described in Example 1 using cyclohexane as solvent and thus obtaining hydrogenated Bisphenol A with practically quantitative yield (higher than 99.5%).

By the gas chromatographic analysis of the crude reaction product the isomeric composition was found to be as follows: 56.8% trans-trans; 36.1% cis-trans; 7.1% cis-cis.

EXAMPLE 7

Operating as described in Example 1, using ter.butyl-methyl ether as solvent, hydrogenated Bisphenol A having the following isomeric composition (gas chromatographic analysis of the crude reaction product) 58.8% trans-trans; 33.3% cis-trans; 6.9% cis-cis, was obtained.

EXAMPLE 8

Operating as described in Example 1 using ethanol as solvent, hydrogenated Bisphenol A having the following isomeric composition (gas chromatographic analysis of the crude reaction product) 59.8% trans-trans; 34.7% cis-trans; 5.5% cis-cis, was thus obtained.

EXAMPLE 9

This example is performed as described in Example 1 using a catalyst (palladium on 5% carbon containing 50% water) basic-washed with a solution containing 1.5% b.w. of sodium carbonate. Hydrogenated Bisphenol A is obtained showing the following isomeric composition (gas chromatographic analysis of the crude reaction product) 65.4% trans-trans; 30.1% cis-trans; 4.5% cis-cis.

What is claimed is:

1. A process for the hydrogenation of bisphenol having the formula

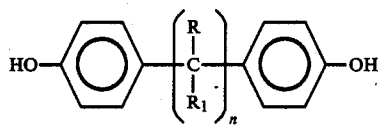
(I)

wherein R and $R_1$, equal to or different from each other, are hydrogen or $C_1$–$C_{10}$ alkyl radicals, and n is 0 or 1, to a product having the formula:

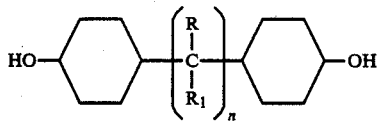
(I')

wherein R, $R_1$ and n have the above meanings, with a content of trans-trans isomer in the product higher than 55% by weight and a reaction selectivity higher than 99% by weight, said process comprising reacting the compound (I), in bulk or in a solvent, with hydrogen in the presence of a catalytic system consisting essentially of palladium supported on an activated carbon, at a reaction temperature between activated carbon, at a reaction temperature between 80° and 160° C.

2. A process according to claim 1, wherein the activated carbon has a specific surface lower than 1000 $m^2/g$.

3. A process according to claim 2, wherein the activated carbon has an specific surface between 400 and 900 $m^2/g$.

4. A process according to claim 2, wherein the activated carbon has an specific surface between 600 and 800 $m^2/g$.

5. A process according to claims 1, 2, 3 or 4, wherein the catalytic system has a pH higher than 7 in water.

6. A process according to claims 1, 2, 3 or 4, wherein the content of palladium in the catalytic system is between 1 and 20% by weight calculated on the dry catalyst.

7. A process according to claims 1, 2, 3 or 4, wherein the bisphenol is 2,2-bis(4-hydroxyphenyl) propane or 4,4'-dihydroxydiphenyl.

8. A process according to claim 1, wherein the solvent is selected from the class consisting of ethyl acetate, methyl-tert.butyl-ether and ethanol, either alone or additioned with water up to 2% by volume and cyclohexane.

9. A process according to claims 1, 2, 3 or 4 wherein the reaction of the bisphenol with hydrogen is carried out at a hydrogen pressure between 50 and 150 atmospheres.

10. A process according to claims 1, 2, 3 or 4 wherein the reaction of the bisphenol with hydrogen is carried out at a hydrogen pressure between 80 and 120 atmospheres.

* * * * *